US005618317A

United States Patent [19]

Träubel et al.

[11] Patent Number: 5,618,317

[45] Date of Patent: Apr. 8, 1997

[54] BISULFITE-BLOCKED POLYISOCYANATES AS TANNING AGENTS

[75] Inventors: Harro Träubel; Helmut Reiff, both of Leverkusen, Germany

[73] Assignee: Bayer Aktiengesellschaft, Leverkusen, Germany

[21] Appl. No.: 456,972

[22] Filed: Jun. 1, 1995

[30] Foreign Application Priority Data

Jun. 28, 1994 [DE] Germany .......................... 44 22 569.5

[51] Int. Cl.$^6$ .............................. C14C 3/22; A61K 7/42; C08G 18/52

[52] U.S. Cl. ......................... 8/94.19 C; 8/94.21; 8/94.33; 424/59; 424/78.08; 528/77

[58] Field of Search .................................. 424/59, 78.08; 8/94.21, 94.19, 94.33; 528/76, 77

[56] References Cited

U.S. PATENT DOCUMENTS

| | | | |
|---|---|---|---|
| 2,923,594 | 2/1960 | Lieberman et al. | 8/94.11 |
| 2,941,859 | 6/1960 | Fein et al. | 8/94.33 |
| 4,106,898 | 8/1978 | Träubel et al. | 8/94.33 |
| 4,413,997 | 11/1983 | Milligan et al. | 8/94.21 |

FOREIGN PATENT DOCUMENTS

| | | |
|---|---|---|
| 278278 | 8/1988 | European Pat. Off. . |
| 72981 | 4/1893 | Germany . |

*Primary Examiner*—Shelley A. Dodson
*Attorney, Agent, or Firm*—Joseph C. Gil; Richard E. L. Henderson

[57] ABSTRACT

The present invention relates to tanning agents containing carbamoyl sulfonate groups that are prepared by the reaction of (A) organic polyisocyanates, (B) 0.01 to 0.4 equivalents, relative to the isocyanate groups of polyisocyanate (A), of polyether alcohols having incorporated polyalkylene oxide units (the equivalents of the polyether alcohol being based on the hydroxyl groups), wherein 40 to 100 mole-% of the polyalkylene oxide units consist of polyethylene oxide units having a sequence length of 5 to 70, (C) optionally, NCO-reactive components other than polyether polyol (B), and (D) ammonium or alkali bisulfites or disulfites.

9 Claims, No Drawings

BISULFITE-BLOCKED POLYISOCYANATES AS TANNING AGENTS

BACKGROUND OF THE INVENTION

This invention relates to the use of bisulfite-blocked polyisocyanates as tanning agents.

Tanning converts animal skins into leather by crosslinking the collagen. One of the most important characteristics of leather is an elevated shrinkage temperature compared with untanned skins, that is, an enhanced resistance to hot water and a white (non-transparent, non-pigmented) appearance after drying.

The type of tanning that is currently becoming increasingly dominant is chrome tanning, in which chromium (III) compounds, under the influence of $OH^-$ ions, provide a crosslinking effect by forming covalent bonds with the carboxyl groups of the collagen. In contrast, the hydrogen bonds to the amide groups of the collagen that can be obtained with polyfunctional vegetable tanning agents are much weaker, which also results in a shrinkage temperature that is only moderately increased. Aliphatic aldehydes, such as glutaraldehyde, which cause crosslinking via the primary amino groups of the collagen, have also been recommended as tanning agents (U.S. Pat. No. 2,941,859). However, the resultant aldimines can undergo a reversible reaction in the presence of water to again form aldehyde and amine.

It has not been possible in practice to use aliphatic diisocyanates, such as hexamethylene diisocyanate (German Patentschrifi 72,981), for toxicological reasons.

The use of bisulfite-blocked aliphatic, cycloaliphatic, or aromatic diisocyanates such as hexamethylene diisocyanate, isophorone diisocyanate, and toluene diisocyanate as tanning agents, as recommended in U.S. Pat. Nos. 2,923,594 and 4,413,997, produces light, non-fading leather, but the tanning liquors are not pH stable.

It has surprisingly now been found that the use of bisulfite-blocked polyisocyanates containing polyethylene oxide groups provides unforeseen advantages relating to commercial application.

SUMMARY OF THE INVENTION

The present invention, therefore, relates to tanning agents comprising reaction products containing carbamoyl sulfonate groups of (A) organic polyisocyanates, (B) 0.01 to 0.4 equivalents, relative to the isocyanate groups of polyisocyanate (A), of a polyether alcohol having incorporated polyalkylene oxide units (the equivalents of the polyether alcohol being based on the hydroxyl groups), wherein 40 to 100 mole-% (preferably 50 to 100 mole-%) of the polyalkylene oxide units consist of polyethylene oxide units having a sequence length of 5 to 70 (preferably 6 to 60, more preferably 7 to 40), (C) optionally, NCO-reactive components other than polyether alcohol (B), and (D) ammonium or alkali bisulfites or disulfites.

The reaction products to be used according to the invention can be obtained by preparing an intermediate NCO-containing product from components (A), (B), and optionally (C), said intermediate product having an NCO content of 3 to 50 (preferably 5 to 45 and more preferably 20 to 45) weight percent, based on the intermediate product, and subsequently blocking the free isocyanate groups of the intermediate product. The products according to the invention thus contain 9.7 to 78 (preferably 14 to 74, more preferably 46.5 to 74) weight percent, calculated as the sodium salt and based on the solid, of carbamoyl sulfonate groups.

DETAILED DESCRIPTION OF THE INVENTION

Aliphatic, cycloaliphatic, araliphatic, aromatic, or heterocyclic polyisocyanates, such as those described, for example, by W. Siefken in *Liebigs Annalen der Chemie,* 562, 75 to 136, are suitable as the organic polyisocyanates (A).

Preferred polyisocyanates (A) comprise compounds of the formula $Q(NCO)_n$ having an average molecular weight less than 800, wherein n represents a number that is at least 2 (preferably 2 to 4) and Q represents an aliphatic $C_4$–$C_{12}$ hydrocarbon group, a cycloaliphatic $C_6$–$C_{15}$ hydrocarbon group, an araliphatic $C_7$–$C_{15}$ hydrocarbon group, or a heterocyclic $C_2$–$C_{12}$ group having 1 to 3 hetero atoms from the series comprising oxygen, sulfur, nitrogen. Examples of such polyisocyanates include (i) diisocyanates such as ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3- and -1,4-diisocyanate and also any mixtures of these isomers, 1-isocyanato-2-isocyanatomethylcyclopentane, 1-isocyanato-3,3,5-trimethyl-5-isocyanatomethylcyclohexane, hexahydrotoluene-2,4- and 2,6-diisocyanate as well as any mixtures of these isomers, hexahydro-1,3- and/or 1,4-phenylene diisocyanate, perhydro-2,4'- and/or -4,4-diphenylmethyl diisocyanate, phenylene-1,3-and 1,4-diisocyanate, toluene-2,4-and 2,6-diisocyanate as well as any mixtures of these isomers, diphenylmethane-2,4'-and/or -4,4'-diisocyanate, naphthalene-1,5-diisocyanate, polyisocyanates containing uretdione groups, such as bis(6-isocyanatohexyl)uretdione or dimers of 1-isocyanato-3,3,5-trimethyl-5-isocyanatomethylcyclohexane containing the uretdione structure, and any mixtures of the aforementioned polyisocyanates; (ii) trifunctional polyisocyanates and polyisocyanates of higher functionality such as the isomers of the triisocyanatotriphenylmethane series (such as triphenylmethane-4,4',4'-triisocyanate) and mixtures thereof; and (iii) compounds prepared by allophanate formation, trimerization, or biuret formation from polyisocyanates (i) and/or (ii) and containing at least 3 isocyanate groups in their molecule. Examples of polyisocyanates prepared by trimerization include the trimer of 1-isocyanato-3,3,5-trimethyl-5-isocyanatomethylcyclohexane that can be obtained by isocyanate formation, and polyisocyanates containing isocyanurate groups that can be obtained by the trimerization of hexamethylene diisocyanate, optionally in admixture with 2,4'-diisocyanatotoluene. Examples of polyisocyanates prepared by biuret formation include tris(isocyanatohexyl)biuret and mixtures thereof with its higher homologs, which can be obtained, for example, according to German Offenlegungsschrift 2,308,015.

Particularly preferred polyisocyanates (A) are those having a molecular weight from 140 to 400 and which contain NCO groups bonded to aliphatic or cycloaliphatic groups, such as 1,4-diisocyanatobutane, 1,6-diisocyanatohexane, 1,5-diisocyanato-2,2-dimethylpentane, 2,2,4- or 2,4,4-trimethyl-1,6-diisocyanatohexane, 1,3-and 1,4-diisocyanatohexane, 1-isocyanato-3,3,5-trimethyl-5-isocyanatomethylcyclohexane, 1-isocyanato-1-methyl-4-isocyanatomethylcyclohexane, and 4,4'-diisocyanatodicyclohexylmethane, as well as any mixtures of such diisocyanates. Araliphatic polyisocyanates may also be used, such as xylylene diisocyanates corresponding to the formulas:

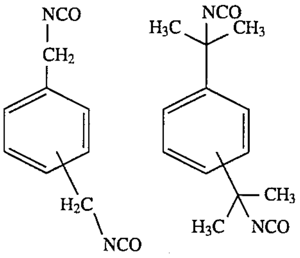

The above-mentioned diisocyanates are preferred but it is also possible to use such diisocyanates in conjunction with monofunctional aliphatic isocyanates, such as butyl isocyanate, hexyl isocyanate, cyclohexyl isocyanate, stearyl isocyanate, or dodecyl isocyanate.

It is also possible to include polyisocyanates having-an average functionality of 2.2 to 4.2. Such polyisocyanates of higher functionality preferably substantially comprise polyisocyanate mixtures consisting of trimeric 1,6-diisocyanatohexane or 1-isocyanato-3,3,5-trimethyl-5-isocyanatomethylcyclohexane and, optionally, dimeric 1,6-diisocyanatohexane or 1-isocyanato-3,3,5-trimethyl-5-isocyanatomethylcyclohexane and the corresponding higher homologs, which contain isocyanurate groups and, optionally, uretdione groups, which have an NCO content of 19 to 24 weight percent, such as those that can be obtained by catalytic trimerization as known in the art and by the formation of isocyanurate from 1,6-diisocyanatohexane or 1-isocyanato-3,3,5-trimethyl-5-isocyanatomethylcyclohexane, and which preferably have an (average) NCO functionality of 3.2 to 4.2.

Other suitable polyisocyanates (A) include polyisocyanates prepared by the modification of aliphatic or cycloaliphatic diisocyanates and which contain a uretdione and/or isocyanurate, urethane and/or allophanate, biuret, or oxadiazine structure, such as those described, for example, in German Offenlegungsschrifien 1,670,666, 3,700,209, and 3,900,053 and European Patent Applications 336,205 and 339,396. Suitable polyisocyanates also include polyisocyanates containing ester groups, such as the tetra- or triisocyanates, which are obtainable by the reaction of pentaerythritol- or trimethylolpropane silyl ethers with isocyanatocaproic acid chloride (see German Offenlegungsschrifi 3,743,782). In addition, it is also possible to use triisocyanates such as tris(isocyanatodicyclohexyl)methane. The quantities of isocyanates that are monofunctional or that have a functionality greater than two are preferably restricted to maximum amounts of 10 mole-% each, based on the total polyisocyanate (A). However, the aforementioned aliphatic, cycloaliphatic, and araliphatic diisocyanates are particularly preferred.

The polyether alcohols (B) are obtainable by methods known in the art by the alkoxylation of suitable starter molecules. Any monohydric or polyhydric alcohols with a molecular weight from 32 to 250 can be used as starter molecules for the preparation of the polyether alcohols. Monofunctional aliphatic $C_1$–$C_8$ alcohols, preferably $C_1$–$C_4$ alcohols, are preferred as the starter molecules. The use of methanol, butanol, ethylene glycol monomethyl ether, or ethylene glycol monobutyl ether as the starter is particularly preferred.

Alkylene oxides that are suitable for the alkoxylation reaction preferably include ethylene oxide and propylene oxide, which can be used in any sequence during the alkoxylation reaction. Any other epoxides, such as butylene oxide, dodecene oxide, or styrene oxide, can also be used in conjunction with ethylene oxide and propylene oxide. Pure polyethylene oxide alcohols are particularly preferred.

Polyalkylene oxide alcohols containing ester groups may also be used in conjunction with alkylene oxides. Suitable polyalkylene oxide alcohols that contain ester groups comprise polyester ethers having terminal OH groups and an average molecular weight less than 10,000 (preferably less than 3000) and obtainable by the reaction of aliphatic $C_2$–$C_8$ dicarboxylic acids or their esters or acid chlorides with polyethers such as polyethylene oxides, polypropylene oxides, or their mixtures, or mixed polyethers, wherein 0.8 to 0.99 equivalents of carboxyl groups or their derivatives are used per OH equivalent of the polyether.

Components (C), which are reactive towards NCO and which are optionally used in conjunction with isocyanate-reactive component (B), include the usual monofunctional to tetrafunctional components used in polyurethane chemistry, such as alcohols, amines, amino alcohols, and mercaptans having molecular weights less than 6000 (preferably less than 2000), including, for example, polyesters, polyether esters, and polycarbonates, provided that such compounds do not fall within the definition of component (B).

Preferred components (C) comprise long chain so-called fatty alcohols or fatty amines, which may optionally be branched, having a fatliquoring or post-fatliquoring action and containing 12 to 30 carbon atoms, as well as hydroxyl-containing esters of natural fatty acids such as stearic acid, oleic acid, palmitic acid, linoleic acid, linolenic acid, and the like. Components (C) that are particularly preferred include natural fats and oils containing OH groups, such as castor oil.

The reaction products of components (A) to (D) that are used according to the invention may contain up to 20 weight percent of incorporated groups of component (C).

Blocking agents (D) include ammonium or alkali bisulfites or ammonium or alkali disulfites. Preferred blocking agents (D) preferably include the sodium salts of sulfurous or disulfurous acids, that is, sodium hydrogen sulfite ($NaHSO_3$; also known as sodium bisulfite) or sodium disulfite ($Na_2S_2O_5$; also known as sodium pyrosulfite or sodium metabisulfite). It is also often advantageous to use other alkali and ammonium salts of these acids, namely potassium bisulfite, potassium disulfite, lithium bisulfite, lithium disulfite, ammonium bisulfite or ammonium disulfite, as well as simple tetraalkylammonium salts of these acids, such as tetramethylammonium bisulfite, tetraethylammonium bisulfite, and the like. For blocking, the salts are preferably used as aqueous solutions with solids contents of 5 to 40 weight percent.

The reaction products used according to the invention can be prepared as follows, for example:

In a first step the polyisocyanate is allowed to react with the polyether alcohol (B) until all the OH groups have been urethanized. The prepolymer containing terminal NCO groups that is prepared in this manner is then blocked by reaction with an alkali or ammonium bisulfite or disulfite in a second step until all the NCO groups have reacted.

The entire process is most preferably carried out in the absence of solvent as a one-pot process. The first step reaction is conducted within a temperature of up to 130° C. (preferably in the range between 50° C. and 120° C., most preferably between 80° C. and 110° C.). This reaction can be followed by titration of the NCO content or by the measurement of IR spectra and evaluation of the carbonyl bands at about 2100 $cm^{-1}$ and is complete when the isocyanate content is no longer more than 0.1 weight percent greater than the value that should be obtained for complete conversion. Reaction times less than four hours are usually sufficient.

The reaction can be speeded up by the use of catalysts such as dibutyltin dilaurate, tin(II) octoate or 1,4-diazabicyclo[2.2.2]octane in amounts of 10 to 1000 ppm based on the reaction components. The NCO prepolymers obtained in this manner, which have NCO contents of 5 to 45 weight percent, are then allowed to react with aqueous solutions of alkali or ammonium sulfites and water in a second step at 0° to 60° C. (preferably 10° to 40° C.) until all the NCO groups have reacted. Reaction times of 1 to 12 hours (preferably 3 to 8 hours) are generally necessary for this purpose. The final products are optically transparent aqueous solutions or, in a few individual cases, stable emulsions of fine particles with average particle diameters of less than 8000 nanometers. It may be advantageous to carry out an initial reaction of the NCO prepolymers with 20 to 50 weight percent of aqueous solutions of alkali or ammonium bisulfites or disulfites, followed by addition of the remaining water after 5 to 45 minutes, so as to obtain a solids content of 10 to 50 weight percent (preferably 25 to 40 weight percent) of the aqueous preparations.

To obtain the tanning effect the products must be made basic; that is, the pH should be at least 7.5, up to a preferred maximum of 9.5. Under these conditions the capped isocyanate groups react, with crosslinking of the collagen (with simultaneous cleavage of the bisulfite group).

All the known basifying agents that are normally used in tanning are suitable for basifying the reaction products according to the invention, such as sodium carbonate and sodium hydrogen carbonate, magnesium oxide, dolomite, tertiary amines, and the like. It is also generally possible (but uncommon) to make controlled additions of sodium or potassium hydroxide. Magnesium oxide is particularly preferred.

A low pH, as is customary in mineral tanning, for example, is not required when tanning with the reaction products used according to the invention. The addition of salt ("pickle") can therefore be avoided. The dehaired skin (i.e., smoothed skin) is delimed down to a pH of 5 to 8 (preferably around 7), the reaction product to be used according to the invention is added, and basification is commenced after a processing time of about one hour (if calcined magnesium oxide is used, this can be added immediately). Depending on the mechanical tumbling action and on the thickness and the digestion (e.g., enzymatic) of the pelt, the tanning operation, and preferably the basification that takes place simultaneously, can be completed in 4 to 6 hours. However, in general—as is customary in chrome tanning—after preliminary processing for one hour and after addition of the basification agent in an additional two stages (each after a processing time of one hour), the process is allowed to run overnight, rinsing is carried out the next morning, and the operation proceeds as usual thereafter.

The reaction products used according to the invention can be used as a replacement for mineral tanning agents. Amounts of 1 to 20 weight percent (preferably 3 to 15 weight percent), based on the weight of pelt, are generally used. In this respect, leathers tanned with the reaction product, which have shrinkage temperatures above 70° C. (preferably above 75° C.) serve as a preliminary stage (analogous to wet blue) for a subsequent tanning operation using synthetic organic polymers (including resin tanning agents) or vegetable tanning agents. The leathers can, of course, still be dyed and grease-impregnated. Tanning using the reaction products to be employed according to the invention proceeds particularly well at pH values of 4 to 10 (preferably 5 to 8). In this respect, neither pickling nor curing have to be carried out. Curing may be advantageous in order to obtain a softer leather; pickling also does no harm.

The reaction products to be used according to the invention can be employed so that tanning is effected simply to obtain a shrinkage temperature of 65° to 70° C. This produces a colorless leather ("wet white") that can then be mineral tanned and can be subsequently tanned using synthetic organic polymers or vegetable tanning agents.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight and relate to de-haired skin/leather.

EXAMPLES

Polyether alcohols (B) used in the Examples

Polyether 1: an ethylene oxide propylene oxide polyether having a molecular weight 2250 and an ethylene oxide group content of 85%, started on n-butanol Polyether 2: an ethylene oxide polyether having a molecular weight 500 and an ethylene oxide group content of 93.6%, started on methanol Polyether 3: an ethylene oxide polyether having a molecular weight 750 and an ethylene oxide group content of 95.7%, started on methanol Polyether 4: an ethylene oxide propylene oxide polyether having a molecular weight 350 and an ethylene oxide group content of 90.9%, started on methanol Polyether 5: an ethylene oxide polyether having a molecular weight 1200 and an ethylene oxide group content of 90.3%, started on oxetane Polyether 6: an ethylene oxide propylene oxide polyether having a molecular weight 3215 and an ethylene oxide group content of 70%, started on propylene glycol Polyether 7: an ethylene oxide propylene oxide polyether having a molecular weight 3100 and an ethylene oxide group content of 70%, started on propylene glycol Polyether 8: an ethylene oxide propylene oxide polyether having a molecular weight 1400 and an ethylene oxide group content of 52%, started on n-butanol Polyether 9: an ethylene oxide propylene oxide mixed bulk polyether having a molecular weight 1400 and an ethylene oxide group content of 44%, started on n-butanol Polyether 10: an ethylene oxide propylene oxide polyether having a molecular weight 4450 and an ethylene oxide group content of 73%, started on glycerin Polyether 11: an ethylene oxide polyether having a molecular weight 1000 and an ethylene oxide group content of 100%, started on ethylene glycol Polyether 12: an ethylene oxide polyether having a molecular weight 1200 and an ethylene oxide group content of 81%, started on nonylphenol Polyether 13: an ethylene oxide propylene oxide polyether having a molecular weight 2000 and an ethylene oxide group content of 85%, started on ethylene glycol Polyether 14: an ethylene oxide propylene oxide polyether having a molecular weight 6200 and an ethylene oxide group content of 45%, started on ethylenediamine Polyether 15: an ethylene oxide polyether having a molecular weight 760 and an ethylene oxide group content of 71%, started on nonylphenol Polyether 16: an ethylene oxide propylene oxide polyether having a molecular weight 4000 and an ethylene oxide group content of 30%, started on propylene glycol Polyether 17: an ethylene oxide propylene oxide polyether having a molecular weight 2000 and an ethylene oxide group content of 49%, started on propylene glycol Polyether 18: an ethylene oxide propylene oxide polyether having a molecular weight 2440 and an ethylene oxide group content of 42%, started on n-butanol Polyether 19: an ethylene oxide propylene oxide polyether having a molecular weight 1840 and an ethylene oxide group content of 45%, started on n-butanol Preparation of the reaction products for use according to the invention .

Example 1

68 g (1.00 mole) of hexamethylene diisocyanate ("HDI") were mixed with 25 g (0.05 moles) of polyether 2 at room temperature and heated to 100° C. This temperature was maintained for 2 hours and the NCO content was then determined (calculated: 42.4%; found: 41.9%). After cooling to 15° C., the product was mixed with 509 g ( 1.91 moles) of 39% aqueous sodium hydrogen sulfite solution and stirred for a further 30 minutes, whereupon the temperature rose to about 45° C. The solids content was then adjusted to 40% with 276 ml of deionized water. After stirring for 7 hours at room temperature, a water-white solution having a pH of 5.8 was obtained.

Examples 2 to 15

The following Examples 2–15 are presented in tabular form:

| Example | Polyisocyanate | Moles polyisocyanate | Polyether | Moles polyether | Moles bisulfite | % of blocked NCO |
|---|---|---|---|---|---|---|
| 2 | HDI | 1.0 | 4 | 0.114 | 1.910 | 37.3 |
| 3 | HDI | 1.0 | 4 | 0.027 | 1.980 | 42.4 |
| 4 | HDI | 0.673 | 1 | 0.015 | 1.436 | 30.5 |
| 5 | HDI | 0.877 | 1 | 0.007 | 1.900 | 40.2 |

-continued

| Example | Polyisocyanate | Moles polyisocyanate | Polyether | Moles polyether | Moles bisulfite | % of blocked NCO |
|---|---|---|---|---|---|---|
| 6 | HDI | 1.0 | 5 | 0.021 | 2.150 | 42.6 |
| 7 | HDI | 0.5 | 8 | 0.0364 | 1.03 | 29.2 |
| 8 | HDI | 0.5 | 6 | 0.078 | 1.082 | 42.8 |
| 9 | HDI | 0.5545 | 10 | 0.0125 | 1.151 | 29.3 |
| 10 | HDI | 0.5871 | 11 | 0.0514 | 1.157 | 29.5 |
| 11 | HDI | 0.2692 | 12 | 0.0225 | 0.537 | 28.4 |
| 12 | HDI | 0.5634 | 13 | 0.0277 | 1.122 | 28.6 |
| 13 | HDI | 0.5 | 14 | 0.0085 | 1.102 | 28.8 |
| 14 | HDI | 0.2688 | 15 | 0.0376 | 0.528 | 28.8 |
| 15 | HDI | 0.500 | 7 | 0.078 | 1.089 | 43.1 |

Examples 16 to 25

Other diisocyanates were used in the following Examples 16–25 (preparation is analogous to that of Example 1). The terms used in the table have the following meanings:

IPDI: Isophorone diisocyanate

HMDI: 4,4 '-Diisocyanatodicyclohexylmethane

XDI: Xylylene diisocyanate (1:1 mixture of the 1,3- and 1,4-isomers)

IMCI: 4-1socyanatom ethyl- 1-methyl- 1-isocyanatocyclohexane

TMHDI: Trimethyl-1,6-diisocyanatohexane (mixture of isomers)

| Example | Polyisocyanate | Moles polyisocyanate | Polyether | Moles polyether | Moles bisulfite | % of blocked NCO |
|---|---|---|---|---|---|---|
| 16 | IPDI | 0.5 | 1 | 0.0113 | 1.077 | 30.3 |
| 17 | IPDI | 0.5 | 1 | 0.0172 | 1.048 | 27.0 |
| 18 | IPDI | 0.436 | 2 | 0.4066 | 0.430 | 5.5 |
| 19 | HMDI | 0.420 | 3 | 0.120 | 0.582 | 11.1 |
| 20 | HMDI | 0.366 | 2 | 0.208 | 0.493 | 9.4 |
| 21 | HMDI | 0.310 | 2 | 0.238 | 0.310 | 5.9 |
| 22 | HMDI | 0.422 | 2 | 0.380 | 0.400 | 5.0 |
| 23 | XDI | 0.500 | 1 | 0.025 | 1.010 | 27.2 |
| 24 | TMHDI | 0.4 | 8 | 0.0364 | 0.831 | 23.5 |
| 25 | IMCI | 0.500 | 1 | 0.025 | 1.010 | 26.6 |

Examples 26 to 36

The following Examples 26-36 contain an additive component (C) or 10 mole-% of trimerized HDI (22.1% NCO). Preparation is analogous to that of Example 1.

Components (C) in the Table represent the following:

A: n-Dodecanol

B: n-Butanol

C: Stearylamine

D: Castor oil

E: Mixture of $C_{12}$–$C_{18}$ fatty alcohols

| Example | Polyisocyanate | Moles polyisocyanate | Polyether | Moles polyether | Moles bisulfite | Component (C) | Grams component (C) | % of blocked NCO |
|---|---|---|---|---|---|---|---|---|
| 26 | HDI | 0.262 | 12 | 0.047 | 0.433 | A | 17 | 17.0 |
| 27 | HDI | 0.212 | 12 | 0.047 | 0.191 | B | 11 | 7.9 |
| 28 | HDI plus trim. HDI | 0.120 0.012 | 5 | 0.059 | 0.228 | — | — | 8.7 |
| 29 | HDI plus | 0.095 | 5 | 0.063 | 0.152 | — | — | 5.8 |

-continued

| Example | Polyiso-cyanate | Moles polyiso-cyanate | Poly-ether | Moles poly-ether | Moles bisulfite | Compo-nent (C) | Grams compo-nent (C) | % of blocked NCO |
|---|---|---|---|---|---|---|---|---|
| | trim. HDI | 0.009 | | | | | | |
| 30 | HDI | 0.328 | 12 | 0.028 | 0.626 | C | 5.2 | 23.9 |
| 31 | HDI | 0.221 | 5 | 0.039 | 0.210 | D | 16 | 9.3 |
| 32 | HDI | 0.179 | 12 | 0.047 | 0.232 | E | 13.4 | 9.0 |
| 33 | HDI | 0.211 | 1 | 0.025 | 0.390 | C | 14.1 | 14.9 |
| 34 | HDI | 0.217 | 8 | 0.036 | 0.390 | C | 13.9 | 14.9 |
| 35 | HDI | 0.218 | 5 | 0.040 | 0.373 | C | 13.8 | 14.4 |
| 36 | HDI plus trim. HDI | 0.139 0.0139 | 5 | 0.0538 | 0.2983 | — | — | 11.4 |

Examples 37 to 45

The following Examples 37–45 are all based on HDI and were prepared analogously to Example 1. Components (C) are defined as for Examples 26–36.

| Example | Polyiso-cyanate | Moles polyiso-cyanate | Poly-ether | Moles poly-ether | Moles bisulfite | Compo-nent (C) | Grams compo-nent (C) | % of blocked NCO |
|---|---|---|---|---|---|---|---|---|
| 37 | HDI | 0.477 | 16 | 0.013 | 1.005 | — | — | 29.5 |
| 38 | HDI | 0.554 | 19 | 0.031 | 1.155 | — | — | 29.4 |
| 39 | HDI | 0.548 | 18 | 0.024 | 1.174 | — | — | 29.9 |
| 40 | HDI | 0.599 | 17 | 0.274 | 1.161 | — | — | 29.8 |
| 41 | HDI | 0.262 | 12 | 0.047 | 0.433 | — | — | 16.6 |
| 42 | HDI | 0.221 | 12 | 0.039 | 0.210 | — | — | 8.0 |
| 43 | HDI | 0.219 | 5 | 0.040 | 0.373 | D | 13.8 | 14.3 |
| 44 | HDI | 0.215 | 5 | 0.044 | 0.377 | D | 9.8 | 14.4 |
| 45 | 1:1 Mixture of products of Exs. 37 & 42 | 0.349 | 16 & 12 (resp.) | 0.026 | 0.607 | — | — | 18.8 |

Application Examples

Auxiliary processing agents used in the Application Examples

TANIGAN BN a synthetic organic substitute tanning agent based on dioxydiphenylsulfone and naphthalenesulfonic acid, acid number 85; manufactured by Bayer AG (Leverkusen)

TANIGAN CH-N a preliminary tanning agent for vegetable tanning based on components analogous to those of TANIGAN BN, acid number 15; manufactured by Bayer AG (Leverkusen)

TANIGAN OS an analogously synthesized substitute tanning agent, acid number of 32; manufactured by Bayer AG RETINGAN R7 an anionic resin tanning agent having a selective filling action and based on dicyanodiamide; manufactured by Bayer AG BAYCHROM A a self-basifying chrome tanning agent containing 21% chromium oxide; manufactured by Bayer AG Quebracho commercially available vegetable tanning agent Mimosa commercially available vegetable tanning agent Chestnut commercially available vegetable tanning agent Polyzym 202 a pancreas-based proteolytic drenching agent; manufactured by Diamant Pelastol PL a combination of synthetic oils for oiling leather; manufactured by Zschimmer & Schwarz GmbH & Co. (Lahnstein)

Pelastol ES a sulfonate of a synthetic oil from Zschimmer & Schwarz GmbH & Co.

Provol BA a combination of natural phospholipids with synthetic softeners

Example A-1

About 100 g of conditioned, de-haired cowhide pelt was pretreated for one hour with the reaction products from the previous Examples according to the invention in 100% liquor. One third of the given amount of magnesium oxide and one third of the given amount of reaction product were then added at hourly intervals in each case, followed by tumbling for 24 hours. The leathers were then rinsed briefly, squeezed out, and dried at room temperature. The shrinkage temperature according to DIN 53,336 was determined on the moist leather. The pH values given in the following Table were obtained.

| Percent reaction product from Example 11 | MgO (g) | pH | Shrinkage temp. (°C.) | Appearance |
|---|---|---|---|---|
| 0 | 9 | 7.5 | 65 | transparent |
| 0.75 | 0.25 | 9 | 74 | transparent |
| 1.75 | 0.4 | 9 | 76 | transparent |
| 3 | 0.65 | 9.2 | 79 | transparent to leather-like |
| 5 | 1 | 9.5 | 81 | leather-like |
| 7.5 | 1.5 | 9.5 | 81 | leather-like |
| 10 | 1.7 | 9.3 | 81 | leather-like |
| 15 | 2.3 | 9.1 | 81 | leather-like |

Examples A-2 to A-37

Examples A-2 to A-37 were carried out using a procedure analogous to that of Example A-1. Reaction products varied.

| Example | Reaction product from Example | Percent reaction product | Shrinkage temp. (°C.) | Appearance |
|---|---|---|---|---|
| A-2 | 16 | 10 | 77 | white, filled |
| A-3 | 17 | 10 | 77 | white, filled |
| A-4 | 19 | 10 | 79 | transparent/ white |
| A-5 | 20 | 10 | 77 | transparent/ white |
| A-6 | 21 | 10 | 77 | almost white |
| A-7 | 22 | 10 | 71 | almost white |
| A-8 | 16 | 20 | 80 | white, soft, filled |
| A-9 | 17 | 20 | 73 | white, soft, filled |
| A-10 | 16 | 10 | 73 | white |
| A-11 | 16 | 19 | 73[1] | no improvement |
| A-12 | 16 | 10 | 82 | white, soft |
| A-13 | 4 | 10 | 81 | white |
| A-14 | 5 | 10 | 75 | transparent |
| A-15 | 16 | 10 | 75[2] | hard, filled |
| A-16 | 4 | 10 | 81[2] | hard, filled |
| A-17 | 5 | 10 | 75[3] | hard, filled |
| A-18 | 1 | 5 | 82 | white |
| A-19 | 1 | 10 | 82 | white, somewhat softer |
| A-20 | 1 | 15 | 84 | white, softer |
| A-21 | 1 | 20 | 84 | white, soft |
| A-22 | 1 | 25 | 84 | white, soft |
| A-23 | 7 | 10 | 81 | white, very soft |
| A-24 | 9 | 10 | 80 | white, soft |
| A-25 | 10 | 10 | 80 | white, soft |
| A-26 | 11 | 10 | 79 | white, soft |
| A-27 | 13 | 10 | 81 | white |
| A-28 | 36 | 10 | 79 | white |
| A-29 | 36 | 5 | 75 | transparent |
| Comparison | U.S. Pat. No. 4,413,997, Example 1 | 10 | 69 | transparent |
| A-30 | 11 | 0 | 65 | transparent, hard |
| A-31 | 11 | 0.75 | 74 | transparent, hard |
| A-32 | 11 | 1.75 | 76 | transparent, hard |
| A-33 | 11 | 3 | 79 | white/ transparent, hard |
| A-34 | 11 | 5 | 81 | white |
| A-35 | 11 | 7.5 | 61 | white |
| A-36 | 11 | 10 | 81 | white |
| A-37 | 11 | 15 | 81 | white/ somewhat soft |

(1) 5% TANIGAN BN
(2) 10% TANIGAN BN
(3) 10% vegetable tanning mixture (1:1:1 quebracho/mimosa/chestnut)

Examples A-38 to A-41

The procedure was analogous to that of Example A-1, the reaction product from Example 7 (10% in each case) being used as the active ingredient and the basifying agents used being varied.

| Example | Basifying agent (%) | Final pH reaction | Shrinkage temp. (°C.) | Appearance |
|---|---|---|---|---|
| A-38 | soda (3.4%) | 9.1 | 81 | white, transparent |
| A-39 | $NaHCO_3$ (6.6%) | 9 | 80 | transparent |
| A-40 | triethanolamine (12.4%) | 9 | 76 | transparent |
| A-41 | MgO (2%) | 9 | 83 | white, transparent |

Examples A-42 to A-45

The procedure was analogous to that of Example A-1 (with 5% reaction product), wherein a mixture of water and additive was used instead of water. These Examples show that different types of pretreatment had no significant effect on the result.

| Example | Pretreatment | Shrinkage temp. (°C.) | Appearance |
|---|---|---|---|
| A-42 | none | 82 | white |
| A-43 | pickling: 5% salt, 0.3% HCOOH, 0.7% $H_2SO_4$ | 80 | white |
| A-44 | curing: 5% salt | 82 | white |
| A-45 | greasing: 5% | 80 | white |

Examples A-46 to A-51

The procedure was analogous to Example A-1. Reaction products varied.

| Example | Reaction product from Example | Percent blocked NCO | Percent reaction product | Shrinkage temp. (°C.) | Appearance |
|---|---|---|---|---|---|
| A-46 | 8 | 28.1 | 10 | 79 | transparent, white |
| A-47 | 12 | 28.6 | 10 | 77 | transparent, white |
| A-48 | 37 | 29.5 | 10 | 79 | transparent, white |
| A-49 | 38 | 29.4 | 10 | 80 | transparent, white |
| A-50 | 39 | 29.9 | 10 | 79 | transparent, white |
| A-51 | 40 | 29.8 | 10 | 78 | transparent, white |

Examples A-52 to A-59

The procedure was analogous to that of Example A-1 (with 10% of reaction product in each case).

| Example | Reaction product from Example | Percent blocked NCO | Shrinkage temp. (°C.) | Appearance |
|---|---|---|---|---|
| A-52 | 41 | 16.6 | 78 | transparent, white |
| A-53 | 43* | 8.3 | 78 | transparent, white |
| A-54 | 44* | 5.8 | 79 | transparent, white |
| A-55 | 42 | 8 | 76 | transparent, white |
| A-56 | 43 | 14.3 | 72 | transparent, white |
| A-57 | 44 | 14.4 | 72 | transparent, white |
| A-58 | 7 | 14.4 | 80 | transparent, white |
| A-59 | 45** | — | 77 | transparent, white |

*Containing 10 mole-% biuret of HDI
**1:1 mixture of reaction products from Examples 7 and 42

Examples A-60 to A-65

The procedure was analogous to that of Example A-1 (with 10% of reaction product in each Example).

| Example | Reaction product from Example | Percent blocked NCO | Shrinkage temp. (°C.) | Appearance |
|---|---|---|---|---|
| A-60 | 25 | 23.7 | 75 | white, hard |
| A-61 | 24 | 8 | 80 | white, transparent |
| A-62 | 28 | 5 | 78 | white, transparent |
| A-63 | 29 | 8 | 76 | white, transparent |
| A-64 | 28 | 8.8 | 79 | white, transparent |
| A-65 | 36 | 11.4 | 79 | white, transparent |

Example A-66

A limed, de-haired cowhide was delimed using 100% water (35° C.) and ammonium sulfate. After 30 minutes 1% Polyzym 202 was added and allowed to work for 60 minutes (pH 8), after which the liquor was drained off. Preliminary tanning was carried out using 50% water (30° C.) and 10% of the reaction product from Example 7. 0.5% magnesium oxide was added after 90 minutes and a further quantity of magnesium oxide added after 7 hours. A pH of 7.2 was obtained after the process was allowed to proceed overnight.

A sample had a shrinkage temperature of 68° C., compared with 57° C. for the unprocessed skin.

After the addition of 1.5% of formic acid, the bath was left for a further minutes. The liquor was then drained off, and the skin was washed, tumbled, and folded (which could be carried out very easily). The skin was then split. One half was subjected to a chrome tanning operation, and the other half was subjected to a synthetic vegetable tanning operation.

| Without chrome | With chrome |
|---|---|
| Tanning | Tanning |
| 100% water, 40° C.<br>2% TANIGAN CH-N, 60 minutes (pH 6.0)<br>+5% TANIGAN OS<br>+5% RETINGAN R7<br>+5% Mimosa<br>60 minutes (pH 4.6) | 50% water, 25° C.<br>6% BAYCHROM A, 3 hours at 25° C.; to 40° C. in 4 hours; overnight (pH 5.0) |

-continued

| Without chrome | With chrome |
|---|---|
| Rinsing | First rinsing |
| 100% water (50° C.)<br>+2.6% Pelastol PC<br>+5% Pelastol ES<br>+2% Provol BA<br>45 minutes<br>+0.2% formic acid, 15 minutes (Ts 75° C.)<br>Ts = shrinking temperature | 100% water (40° C.)<br>+2% TANIGAN OS<br>+2% RETINGAN R7<br>+2% Mimosa<br>60 minutes (pH 4) |
| | Second rinsing |
| | 100% water, 50° C.<br>+2.6% Pelasol PC<br>+5% Pelasol ES<br>+Provol BA<br>+0.2% formic acid after 45 minutes a pH of 5 (somewhat too high) was obtained after 15 minutes |

After rinsing, the leathers were unloaded, tumbled, and stretched on a frame overnight. On the following day they were vacuumed, studded, and dried out while suspended. The chrome-free leather was filled and white (similar to the chrome-tanned leather). Both leathers could be dyed very well.

What is claimed is:

1. A tanning agent comprising a reaction product containing carbamoyl sulfonate groups of (A) an organic polyisocyanate, (B) 0.01 to 0.4 equivalents, relative to the isocyanate groups of polyisocyanate (A), of a polyether alcohol having incorporated polyalkylene oxide units, wherein 40 to 100 mole-% of the polyalkylene oxide units consist of polyethylene oxide units having a sequence length of 5 to 70, (C) optionally, NCO-reactive components other than polyether alcohol (B) in an amount such that the reaction product incorporates 0 to 20 weight percent of said NCO-reactive component (C), and (D) an ammonium or alkali bisulfite or disulfite in an amount such that the reaction product of components (A), (B), (C), and (D) contains no free isocyanate groups.

2. A tanning agent according to claim 1 wherein 50 to 100 mole-% of the polyalkylene oxide units consist of polyethylene oxide units.

3. A tanning agent according to claim 1 wherein the sequence length of the polyethylene oxide units is 6 to 60.

4. A tanning agent according to claim 1 wherein the sequence length of the polyethylene oxide units is 7 to 40.

5. A tanning agent according to claim 1 wherein the content of carbamoyl sulfonate groups (calculated as the sodium salt) is 9.7 to 78 weight percent.

6. A tanning agent according to claim 1 wherein the content of carbamoyl sulfonate groups (calculated as the sodium salt) is 14 to 74 weight percent.

7. A process for preparing a tanning agent according to claim 1 comprising (1) preparing an intermediate NCO-containing product having an NCO content of 3 to 50 weight percent, based on said intermediate NCO-containing product, by reacting (A) an organic polyisocyanate, (B) 0.01 to 0.4 equivalents, relative to the isocyanate groups of polyisocyanate (A), of a polyether alcohol having incorporated polyalkylene oxide units, wherein 40 to 100 mole-% of the polyalkylene oxide units consist of polyethylene oxide units having a sequence length of 5 to 70, and (C) optionally, NCO-reactive components other than polyether alcohol (B) in an amount such that the tanning agent incorporates 0 to 20 weight percent of said NCO-reactive component (C), and (2) blocking the free isocyanate groups of the intermediate product by reacting the intermediate product with an ammonium or alkali bisulfite or disulfite.

8. A method for tanning an animal skin comprising sequentially applying to the animal skin (a) a tanning agent according to claim 1 in aqueous medium at a pH of 4 to 10, (b) optionally, a mineral tanning agent, and (c) a synthetic organic polymer tanning agent or vegetable tanning agent.

9. A method for tanning comprising applying a tanning agent according to claim 1 to an animal skin in basic aqueous medium at a pH of at least 7.5.

* * * * *